(12) United States Patent
Prusiner et al.

(10) Patent No.: US 7,151,000 B2
(45) Date of Patent: *Dec. 19, 2006

(54) METHOD OF CONCENTRATING PROTEINS FROM SERUM

(75) Inventors: Stanley B. Prusiner, San Francisco, CA (US); Jiri G. Safar, Walnut Creek, CA (US)

(73) Assignee: The Regents of the University of California, Oakland, CA (US)

(*) Notice: Subject to any disclaimer, the term of this patent is extended or adjusted under 35 U.S.C. 154(b) by 421 days.

This patent is subject to a terminal disclaimer.

(21) Appl. No.: 10/425,129

(22) Filed: Apr. 28, 2003

(65) Prior Publication Data

US 2003/0208052 A1    Nov. 6, 2003

Related U.S. Application Data

(63) Continuation of application No. 09/670,506, filed on Sep. 26, 2000, now abandoned, which is a continuation of application No. 09/264,148, filed on Mar. 5, 1999, now Pat. No. 6,166,187.

(51) Int. Cl.
*G01N 33/539* (2006.01)

(52) U.S. Cl. ............... 436/539; 435/7.1; 435/173.9; 435/287.2; 435/962; 436/971; 436/518; 436/524; 436/528; 436/536; 436/538; 436/166; 436/174; 436/177; 436/16; 436/17

(58) Field of Classification Search ............ 435/7.1, 435/7.21, 6, 23, 173.9, 287.2, 962, 971; 530/402, 530/403, 412, 419; 436/518, 524, 528, 534, 436/63, 536, 147, 538, 148, 539, 166, 547, 436/174, 175, 176, 177, 811, 825, 16, 17
See application file for complete search history.

(56) References Cited

U.S. PATENT DOCUMENTS 3,780,935 A * 12/1973 Lukacs et al. ............... 233/1
5,419,872 A    5/1995 Montgomery et al.
5,422,284 A    6/1995 Lau
5,750,361 A    5/1998 Prusiner et al.
5,773,572 A    6/1998 Fishleigh et al.
5,834,533 A   11/1998 Prusiner et al.

(Continued)

FOREIGN PATENT DOCUMENTS

WO    WO 98/00441    1/1998

(Continued)

OTHER PUBLICATIONS

Burstein et al., "Rapid method for the isolation of lipoproteins from human serum by precipitation with polyanions" *Journal of Lipid Research* 11:583-595 (1970).

(Continued)

*Primary Examiner*—Long V. Le
*Assistant Examiner*—Gailene R. Gabel
(74) *Attorney, Agent, or Firm*—Karl Bozicevic; Bozicevic, Field & Francis LLP (57) ABSTRACT

A sample is prepared from blood in a manner which makes it possible to further analyze proteins in the sample, e.g. to detect prions in the sample. Blood is extracted, allowed to clot and subjected to separation processing (e.g. centrifugation) to obtain serum. The serum is treated with a complexing agent which agent binds prions in the sample forming an agent/protein complex which makes it possible to concentrate the complex. Concentration of the complex results in a sample which can be successfully analyzed, e.g. assayed using a range of different types of assay methodologies for detecting prions.

15 Claims, 5 Drawing Sheets

U.S. PATENT DOCUMENTS

| | | | |
|---|---|---|---|
| 5,834,593 | A | 11/1998 | Prusiner et al. |
| 5,891,641 | A * | 4/1999 | Prusiner et al. ............... 435/7.1 |
| 5,908,969 | A | 6/1999 | Prusiner et al. |
| 5,977,324 | A * | 11/1999 | Prusiner et al. .............. 530/418 |
| 6,166,187 | A * | 12/2000 | Prusiner et al. .............. 530/419 |

FOREIGN PATENT DOCUMENTS

| | | |
|---|---|---|
| WO | WO 98/23962 | 6/1998 |
| WO | WO 00/43782 | 7/2000 |

OTHER PUBLICATIONS

Safar et al., "Eight prion strains have PrP$^{Sc}$ molecules with different conformations" *Nature Medicine* 4(10):1157-1165 (Oct. 1998).
Warnick et al., "Comparison of Current Methods for High-Density Lipoprotein Cholesterol Quantitation" *Clin. Chem.* 25(4):596-604 (1979).
Castilla et al., "Detection of prions in blood" *Nature Medicine Advance on Line Publishing* pp. 1-4 (Aug. 28, 1995).
Saborio et al., "Sensitive detection of pathological prion protein by cyclic amplification of protein misfolding" *Nature* 411:810-813 (Jun. 14, 2001).
Alpers, M.P., *Slow Transmissible Diseases of the Nervous System*, vol. 1, S.B. Prusiner and W.J. Hadlow, eds. (New York: Academic Press), pp. 66-90 (1979).
Basler et al., *Cell* 46:417-28 (1986).
Bolton et al., *Science* 218:1309-11 (1982).
Brown et al., *Lancet* 340:24-27 (1992).
Buchanan et al., *Br. Med. J.* 302:824-828 (1991).
Cochius et al., *Aust. N.Z. J. Med* 20:592-593 (1990).
Cochius et al., *J. Neurol. Neurosurg. Psychiatry* 55:1094-1095 (1992).
Fradkin et al., *JAMA* 265:880-884 (1991).
Gajdusek et al., *Nature* 209:794-796 (1966).
Gajdusek, D.C., *Science* 197:943-960 (1977).
Gibbs, Jr. et al., *N. Engl. J. Med.* 328:358-359 (1993).
Gibbs, Jr. et al., *Science* 161:388-389 (1968).
Gibbs, Jr. et al., *Slow Transmissible Diseases of the Nervous System*, vol. 2, S.B. Prusiner and W.J. Hadlow, eds. (New York: Academic Press), pp. 87-110 (1979).
Goldfarb et al., *Science* 258:806-808 (1992).
Hadlow, W.J., *Lancet* 2:289-290 (1959).
Harries-Jones et al., *J. Neurol. Neurosurg. Psychiatry* 51:1113-1119 (1988).
Healy et al., *Br. J. Med.* 307:517-518 (1993).
Hsiao et al., *Neurology* 40:1820-1827 (1990).
Kitamoto et al., *Proc. R. Soc. Lond.* 343:391-398.
Klatzo et al., *Lab Invest.* 8:799-847 (1959).
Koch et al., *N. Engl. J. Med.* 313:731-733 (1985).
Lasmezas et al., *Biochem. Biophys. Res. Commun.* 196:1163-1169 (1993).
Locht et al., *Proc. Natl. Acad. Sci. USA* 83:6372-6376 (1986).
McKinley et al., *Cell* 35:57-62 (1983).
Medori et al., *N. Engl. J. Med.* 326:444-449 (1992).
Nisbet et al., *J. Am. Med. Assoc.* 261:1118 (1989).
Pattison, I.H., *NINDB Monograph 2*, D:C. Gajdusek, C.J. Gibbs Jr. and M.P. Alpers, eds. (Washington, D.C.: U.S. Government Printing), pp. 249-257 (1965).
Prusiner et al., *Biochemistry* 21:6942-50 (1982).
Prusiner, S.B., "Molecular biology of prion disease," *Science* 252:1515-1522 (1991).
Scott et al., *Cell* 59:847-857 (1989).
Tateishi et al., *Prion Diseases of Humans and Animals*, Prusiner et al., eds. (London: Ellis Horwood), pp. 129-134 (1992).
Thadani et al., *J. Neurosurg.* 69:766-769 (1988).
Wilesmith, J. and Wells, *Microbiol. Immunol.* 172:21-38 (1991).
Willison et al., *J. Neurosurg. Psychiatric* 54:940 (1991).
*New Scientist*, Jul. 31, 1993, p. 4.
*New Scientist*, Nov. 20, 1993, p. 10.

* cited by examiner

METHOD OF CONCENTRATING PROTEINS FROM SERUM

CROSS-REFERENCES

This application is a continuation of U.S. patent application Ser. No. 09/670,506, filed Sep. 26, 2000 which is a continuation of U.S. patent application Ser. No. 09/264,148, filed Mar. 5, 1999 (now U.S. Pat. No. 6,166,187 issued Dec. 26, 2000) of which application is incorporated herein by reference in its entirety and to which applications we claim priority under 35 U.S.C. §120.

GOVERNMENT RIGHTS

The United States Government may have certain rights in this application pursuant to Grant No. AG02132 awarded by the National Institutes of Health.

FIELD OF THE INVENTION

The invention relates generally to methods of detecting prions in blood.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not readily infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172: 21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., *Science* 197: 943–960 (1977); Medori et al., *N. Engl. J. Med.* 326: 444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* 343:391–398.

Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System*, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into nonhuman primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using nonhuman primates, some cases of human prion disease have been transmitted to rodents but apparently with less regularity [Gibbs, Jr. et al., *Slow Transmissible Diseases of the Nervous System*, Vol. 2, S. B. Prusiner and W. J. Hadlow, eds. (New York: Academic Press), pp. 87–110 (1979); Tateishi et al., *Prion Diseases of Humans and Animals*, Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59:847–857 (1989)]. SHaPrP differs from MoPrP at 16 positions out of 254 amino acid residues [Basler et al., *Cell* 46:417–428 (1986); Locht et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302: 824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH [Gibbs, Jr. et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307:517–518 (1993); Cochius et al., *Aust. N. Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261: 1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10. ) Far greater numbers of people are given blood which is never tested for the presence of prions. In view of such, there is a need for a method for isolating and characterizing prions in blood. The present invention provides such a method.

SUMMARY OF THE INVENTION

The essence of the invention is the preparation of a sample (obtained from blood) in a manner which makes it possible to isolate and characterize and if desired merely detect a disease conformation of a protein (e.g. PrP$^{Sc}$) present in the sample. Whole blood is removed from a patient. The blood is allowed to clot at room temperature and then subjected to centrifugation to separate serum. The separated serum is contacted with a complexing agent such as sodium phosphotungstate (PTA) which binds PrP$^{Sc}$ in the serum thereby making it possible to concentrate any PrP$^{Sc}$ present. The concentrated fraction putatively containing PrP$^{Sc}$ may be further concentrated and the PrP$^{Sc}$ characterized or, if desired merely assayed to determine if PrP$^{Sc}$ is present. Detecting PrP$^{Sc}$ makes it possible to avoid the use of blood contaminated with PrP$^{Sc}$. Surprisingly, when samples are prepared from plasma, platelets, or white blood cells and are tested for the presence of prions negative results are obtained even though positive results were obtained when testing samples prepared from the same blood in accordance with the present invention. Thus, the method disclosed here is an inventive pretreatment method which makes it possible to isolate and characterize and if desired to use one or more different assay methods to detect prions or the pathogenic conformation of another protein present in blood.

A primary object of the invention is to provide a sample preparation methodology which results in unmasking proteins (e.g. prions) which exist in a disease conformation and are present in blood which method makes it possible to isolate and characterize those proteins as they exist in blood as opposed to how the proteins might be characterized within other organs.

Another object of the invention is to provide a method which includes the initial steps needed to reveal a naturally occurring factor inhibitory for prion formation which inhibitory factor could be used in its naturally occurring or modified form as a therapeutic for the treatment of diseases related to disease conformations of certain proteins (e.g. prion diseases).

Another object of the invention is to provide a sample (produced by a method of the invention) which sample can be assayed via a variety of techniques to detect a disease conformation of a protein (e.g. PrP$^{Sc}$) in blood.

An object of the invention is to provide a method for determining if infectious prions (PrP$^{Sc}$) are present in blood.

Another object is to provide a method of confirming a diagnosis of a prion related disease using a blood sample.

An advantage of the invention is that it provides a testable sample which can be assayed for the detection of prions in blood.

A feature of the invention is that only blood serum can be used to carry out the assay to detect PrP$^{Sc}$ i.e. testing blood, plasma, platelets and white blood cells provides false negative results.

Another advantage is that blood, blood products, bone marrow and all other organs and tissues (e.g. used in human transplant operations) can be tested and certified prion free.

Another feature of the invention is that a variety of different complexing agents can be used to concentrate any PrP$^{Sc}$ in the serum to provide the treated sample of the invention prior to testing.

Another feature of the invention is that the complexing agent may be heteropoly acids or metal salts thereof, or biological agents such as peptides, small molecules, selective PrP$^{Sc}$ binding antibodies and PrP binding antibodies.

Another feature is that preferred complexing agents are metal salts of phosphotungstic acid, with sodium phosphotungstate being particularly preferred.

Yet another feature of the invention is that the process allows for prions present in the blood to be unmasked thereby facilitating purification procedures involved in removal of prion infectivity from blood and other organs and/or tissues.

Another object of the invention is to use the sample prepared according to the methodology and thereafter further analyze the protein present in the complex formed in order to determine specific characteristics of the protein including its solubility, three-dimensional structure and infectivity.

An important advantage of the invention is that the pathogenic conformation of the protein can be extracted from blood and then analyzed by comparing it with the same protein extracted from other tissue such as brain tissue.

These and other objects, aspects, advantages, and features of the invention will become apparent to those persons skilled in the art upon reading the details of the methodology as more fully described below.

BRIEF DESCRIPTION OF THE DRAWINGS

FIG. 3 is a graph showing the results of a conformation-dependent immunoassay being carried out on a plasma with the results comparing the control which does not contain prions with samples of plasma collected from animals that are infected with prions and is labeled as "scrapie." The experiment and results are further described in Comparative Example 3.

DETAILED DESCRIPTION OF PREFERRED EMBODIMENTS

Before the present, prepared test samples, methodology and components used therein are disclosed and described, it is to be understood that this invention is not limited to particular samples, methods, steps, complexing agents, proteins, labels, or assays as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

DEFINITIONS

The term "serum" is intended to mean a fraction of blood which is obtained by withdrawing blood from the body and placing the blood in a container without any preservatives and allowing the blood to form clots. The plasma is the liquid portion of the blood which can then be separated away from the clot. Clots are formed by converting of soluble proteins (fibrinogen) into insoluble protein (fibrin). The fibrin forms a spongy network of fibrous material holding the blood corpuscles into a solid mass. Clotting generally takes 10–15 minutes at room temperature but varies depending upon the particular type of blood drawn and the type of container the blood is placed in. In a broad sense the term "serum" is used herein to refer to the non-solid-like material in blood with the clot forming proteins also being eliminated. The difference between serum and plasma is that serum is formed by clotted blood which contains fibrin and plasma which contains fibrinogen is formed from blood that is not allowed to clot because of an anticoagulant. A fibrinogen test can be used to determine if a specimen is serum or plasma. With serum, fibrinogen can be added without obtaining a reaction. Plasma anticoagulated specimens can be centrifuged as soon as they are collected. Serum specimens, blood with no anticoagulant, must be allowed to clot—generally for at least 30 minutes at room temperature. Clotting time can be affected by physical components such as glass or silicon particles and can also be reduced by the addition of thrombin. In order to obtain plasma anticoagulants such as EDTA, sodium citrate (which may be buffered or non-buffered) or heparin are added. For comparative examples 1–3 buffered sodium citrate is used as the anticoagulant. No anticoagulant is used with the methodology of the present invention which requires serum.

The term "complexing agent" is used herein to refer to any material which binds or complexes selectively with either the constrictive conformation of a protein (e.g. with $PrP^{Sc}$) and/or with the relaxed conformation of a protein (e.g. $PrP^{C}$). This complexing agent may be a biological molecule such as a peptide or antibody, e.g. an antibody selective for $PrP^{Sc}$ in any conformation (native or denatured), or a chemical agent, e.g. phosphotungstic acid (PTA), which may be in the form of a salt, e.g. sodium phosphotungstate. The complexing agents may be used singly or in combination. For example, a biological complexing agent may be used in tandem with a chemical complexing agent, such as the use of a peptide and a chemical agent. In another example, two complexing agents of the same class can be used together, e.g. a mixture of phosphotungstic acid (and salts thereof) and trichloroacetic acid. The complex formed must provide some means for separating the complex from the remainder of the composition, such as immobilization of the complexing agent to a surface. For example a complexing agent binds to the desired protein ($PrP^{Sc}$) forming an agent/protein complex which has a higher specific gravity than the protein or agent alone. Accordingly, the agent/protein complex can be separated away via gravity which is preferably supplemental by the use of centrifugation. A preferred complexing agent which binds $PrP^{Sc}$ more readily than it binds $PrP^{C}$ and a particularly preferred agent binds $PrP^{Sc}$ with a high degree of affinity and does not bind $PrP^{C}$ at significant levels. Objectively, a preferred binding agent binds $PrP^{Sc}$ with twice or more the binding affinity as it binds $PrP^{C}$ and preferably five times or more the binding affinity as it binds $PrP^{C}$.

The terms "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have two or more different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the $PrP^{c}$ form and the disease related form referred as the $PrP^{Sc}$. Although a prion protein or the $PrP^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^{C}$ which, under appropriate conditions is converted to the infectious $PrP^{Sc}$ form.

The terms "prion", "prion protein" and "$PrP^{Sc}$ protein" and the like we used interchangeably herein to refer to the infectious $PrP^{Sc}$ form of PrP, and is a contraction of the words "protein" and "infection." Particles are comprised largely, if not exclusively, of $PrP^{Sc}$ molecules encoded by a PrP gene. Prions are generally $PrP^{Sc}$ dimers. Prions are distinct from bacteria, viruses and viroids. Known prions infect animals to cause a prion disease "scrapie," a transmissible, degenerative disease of the nervous system of sheep and goats, as well as "bovine spongiform encephalopathy" (BSE), or "mad cow disease", and "feline spongiform encephalopathy" of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses a PrP protein including known polymorphisms and pathogenic mutations. The term "PrP gene" refers generally to any gene of any species which encodes any form of a PrP protein. Some commonly known PrP sequences are described in Gabriel et al., *Proc. Natl. Acad. Sci. USA* 89:9097–9101 (1992), and U.S. Pat. Nos. 5,565,186; 5,763,740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) or $PrP^{Sc}$ (disease) form.

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Preferred antibodies for assays of the invention are immunoreactive or immunospecific for and therefore specifically and selectively bind to a protein of interest e.g., a PrP protein and specifically a $PrP^{Sc}$ protein or $PrP^{Sc}$ dimer. Antibodies which are immunoreactive and immunospecific for both the native non-disease form and disease form (e.g., for both native $PrP^{C}$ and native $PrP^{Sc}$) may be used. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Pat. No. 5,846,533 issued Dec. 8, 1998 also incorporated herein by reference. The term "antibody" encompasses all types of antibodies, e.g. polyclonal, monoclonal, and those produced by the phage display methodology. Particularly preferred antibodies of the invention are antibodies which have a relatively high degree of affinity for both native $PrP^{C}$ and $PrP^{Sc}$ and those with greater binding affinity for $PrP^{Sc}$ are preferred. An antibody of the invention is a "complexing agent" as defined herein.

An antibody for binding to $PrP^{C}$ is the monoclonal antibody 263K 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No. 4,806,627 issued Feb. 21, 1989—incorporated by reference to disclose antibodies which selectively bind $PrP^{c}$ but not $PrP^{Sc}$ "Purified antibody" refers to that which is sufficiently free of other proteins, carbohydrates, and lipids with which it is naturally associated. Such an antibody "preferentially binds" to $PrP^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native $PrP^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., a $PrP^{Sc}$. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as $PrP^{Sc}$ so that by adjusting binding conditions the antibody binds almost exclusively to an epitope site or fragments of a desired protein such as an epitope fragment of $PrP^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:
CNS for central nervous system;
BSE for bovine spongiform encephalopathy;
CJD for Creutzfeldt-Jacob Disease;
FFI for fatal familial insomnia;
GdnHCl for Guanidine hydrochloride;
GSS for Gerstamnn-Strassler-Scheinker Disease;
Hu for human;
HuPrP for human prion protein;
Mo for mouse;
MoPrP for mouse prion protein;
SHa for a Syrian hamster;
SHaPrP for a Syrian hamster prion protein;
$PrP^{Sc}$ for the scrapie isoform of the prion protein;
$PrP^{C}$ for the cellular contained common, normal isoform of the prion protein;
$PrP^{CJD}$ for the CJD isoform of a PrP protein;
FVB for a standard inbred strain of mice often used in the production of transgenic mice since eggs of FVB mice are relatively large and tolerate microinjection of exogenous DNA relatively well;
$[PrP_\beta]$—concentration of prion protein in β-sheet conformation;
[DRC]—concentration of a disease related conformation of a protein.
PTA—phosphotungstic acid
NaPTA—sodium phosphotungstate
TCA—trichloroacetic acid
AC—affinity chromatography

GENERAL ASPECTS OF THE INVENTION

Assays for the detection of prions are in development but not yet commercialized. Further, the cost, convenience or accuracy (on a large scale) of such assays has not yet been determined. Accordingly, when a material such as human plasma is suspected of containing prions it is destroyed—see The Wall Street Journal, Nov. 25, 1998 page 1 article entitled: "'Mad Cow' Fears Leads U. K. to Destroy Parts of all Donated Blood" indicating that England was destroying their supply of human plasma. This dramatic action was taken because (1) prions might be present in their human plasma, (2) prion diseases are fatal and not treatable at present, (3) there are no commercially available test for prions at present, and (4) no commercially available method of removing prions from a sample at present. The present invention comprises a method for preparing samples in a manner such that they can be further analyzed, e.g. tested for the presence of a disease related conformation of a protein, e.g. $PrP^{Sc}$.

Some proteins such as the protein expressed by the PrP gene have more than one conformational shape. For example a PrP protein may assume its cellular form, i.e. $PrP^{C}$ form or its scrapies form, i.e. $PrP^{Sc}$ form. One form of the protein is harmless (e.g. $PrP^{C}$) whereas another form of the protein is pathogenic (e.g. $PrP^{Sc}$). When the constricted, pathogenic form of the protein such as $PrP^{Sc}$ is present in an animal in very small amounts the animal (e.g. a human, cow, sheep, pig or chicken) is not showing symptoms of disease. However, the animal will develop a disease related to the pathogenic form of the protein—e.g. develop a prion disease. To avoid possible transmission of disease, it is important to determine if any $PrP^{Sc}$ is present in biological fluids, and particularly biological fluids that are to be introduced to a subject (e.g. blood products). The present invention is useful with respect to preparing a sample in a particular manner so that the sample can be assayed to determine if a disease conformation of a protein is present in the sample. If a disease conformation of a protein is detected then the remainder of the blood is destroyed. If no disease conformation of a protein is found then the blood may be used directly, stored or used to produce a derivative blood product.

DISEASES ASSOCIATED WITH INSOLUBLE PROTEINS

Much of the disclosure and the specific examples provided herein relate to the use of the invention to unmark $PrP^{Sc}$ in blood. However, as indicated above, the invention can be applied to characterizing or determining the presence of any protein which assumes two different conformational shapes, one of which is associated with the disease. The following is a non-limiting list of diseases with associated insoluble proteins which assume two or more different conformations.

| Disease | Insoluble Proteins |
|---|---|
| Alzheimer's Disease | APP, Aβ peptide, α1-antichymotrypsin, tan, non-Aβ component |
| Prion diseases, Creutzfeld Jakob disease, scrapie and bovine spongeform encephalopathy | $PrP^{Sc}$ |
| ALS | SOD and neurofilament |
| Pick's disease | Pick body |
| Parkinson's disease | Lewy body |
| Diabetes Type 1 | Amylin |
| Multiple myeloma-- plasma cell dyscrasias | IgGL-chain |
| Familial amyloidotic polyneuropathy | Transthyretin |
| Medullary carcinoma of thyroid | Procalcitonin |
| Chronic renal failure | $β_2$--microglobulin |
| Congestive heart failure | Atrial natriuretic factor |
| Senile cardiac and systemic amyloidosis | Transthyretin |

-continued

| Disease | Insoluble Proteins |
|---|---|
| Chronic inflammation | Serum amyloid A |
| Atherosclerosis | ApoA1 |
| Familial amyloidosis | Gelsolin |

It should be noted that the insoluble proteins listed above each include a number of variance or mutations which result in different strains which are all encompassed by the present. Known pathogenic mutations and polymorphisms in the PrP gene related to prion diseases are given below and the sequences of human, sheep and bovine are given in U.S. Pat. No. 5,565,186, issued Oct. 15, 1996.

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

It should also be noted that such proteins have two different 3-dimensional conformations with the same amino acid sequence. One conformation is associated with disease characteristics and is generally insoluble whereas the other conformation is not associated with disease characteristics and is soluble. The methodology of the present invention is not limited to the diseases proteins and strains listed.

PROCEDURES IN GENERAL

The essence of the present invention is in determining processing steps which allow a sample to be prepared so that the prepared sample can then be further analyzed, e.g. assayed for the presence of a disease conformation of a protein, e.g. assayed for the presence of $PrP^{Sc}$. When the sample is correctly prepared in accordance with the present invention then a variety of different assay methods can be used to detect the protein of interest. However, if the sample is not prepared in accordance with the present invention then known assay methodologies will give false negative results.

Simply stated the invention comprises first obtaining a sample of blood and allowing the blood to clot. Serum is separated away and serum is treated with a complexing agent which forms an agent/protein complex with the protein of interest. The formation of the complex facilitates concentration of the protein of interest, e.g. by increasing its specific gravity so that the complex can be separated away by using a centrifuge and concentrated. At this point the sample is properly prepared and may be further analyzed, e.g. tested for the presence of the protein of interest by any known method or by methods yet to be developed.

The blood used to prepare a sample of the invention can be any blood but is preferably the blood of a human or domestic farm animal e.g. a cow, sheep, goat, horse or chicken. Although it is important for the blood to clot no particular procedure is needed to carry out the clotting. The blood may simply be allowed to stand at room temperature (preferably in a sterile glass container) and observed for clotting. It is, of course, important not to add any anticoagulants, anti-clotting agents etc. or other compound which would prevent clot formation. Proteins in the blood involved in clotting are thereby removed and the removal of these proteins may be critical to sample preparation in that these clot forming proteins may somehow prevent detection of the protein of interest. Once a clot has formed the serum is separated away using any known procedure e.g. centrifugation of the sample until the serum is clearly separate from the clot and the serum can be poured off of the top of the sample.

After the serum is obtained the serum is treated in a manner which allows for the protein of interest to be concentrated. This is preferably done by adding a complexing agent which forms an agent/protein complex which complex has a higher specific gravity than either the complexing agent or protein of interest. Thus, the complex settles out in the sample and the rate of such is greatly enhanced by centrifugation.

END USES

Once the sample has been prepared in accordance with the present invention the sample has a variety of possible end uses. For example, the sample merely can be used in order to carry out further analysis to determine if the protein of interest (e.g. prions) are present in the sample. However, the invention offers a range of other possible end uses. For example, the sample can be used to carry out specific characterization of the protein which has formed a complex with the complexing agent. Characterization of that protein can provide useful information. The characterization can include determining the solubility, three-dimensional structure and infectivity of the protein. These characteristics as well as others can then be compared with the same determined characteristics of that protein extracted from a different organ or tissue such as when the protein is extracted and isolated from brain tissue.

No conclusive assertions can be made here with respect to why the present invention works. Thus, the scope of the present invention is not bound by any particular theory explaining the underlying mechanism. Notwithstanding such it appears as though proteins involved in clot formation have an inhibitory effect on the formation of the pathogenic conformation. Alternatively, the clot forming proteins remove some other inhibitor or factor which allows for the formation of the pathogenic form of the protein. Assuming such is the case, the isolation of this inhibitor would provide a valuable therapeutic for diseases. The inhibitor could be administered to any mammal including a human after first noting the signs of disease related to the pathogenic form of the protein. The administration of such an inhibitor would prevent further formation of the pathogenic formation of the protein and thereby halt progression of the disease.

COMPLEXING AGENTS

In one embodiment, a chemical agent such as a heteropoly acid (e.g. PTA), or preferably a metallic salt thereof (NaPTA) is the complexing agent. The sample is subjected to a the complexing agent over a period of time sufficient to allow substantially all the $PrP^{Sc}$ in the sample to complex with the PTA. For example, the sample could be incubated at about 30° C. to 45° C. (preferably 37° C.) over a period of from about 1 to 16 hours. The complexing agent forms a complex with the $PrP^{Sc}$. What is important is that complex formed can be separated away from the rest of the sample by some means, e.g. filtration, use of magnetic field, sedimentation and the like.

The process of the invention produces a biological sample wherein the $PrP^{Sc}$ or other pathogenic protein is substantially concentrated in the resulting sample.

Compounds which are useful as complexing agents in the present invention include antibodies, enzymes, peptides, chemical species, binding molecules, etc. These complexing agents are used in a manner that allows binding and concentration of prions in serum while maintaining the essential elements of the serum intact, e.g. retention of cellular morphology and protein integrity.

Chemical Agents

In one embodiment of the invention, the compound for removal of prions from a biological material is a chemical agent that precipitates $PrP^{Sc}$. One preferred class of chemical agents for use as complexing agents in the present invention are heteropoly acids and salts thereof. Heteropoly acids are filly or partially protonated forms of oxyanions having at least one central element and at least one coordinating element. Heteropoly acids may have the Keggin or Dawson structures.

A particular class of heteropoly acids is the protonated form of heteropolymolybdates. These anions contain from 2 to 18 hexavalent molybdenum atoms around one or more central atoms. About 36 different elements have been identified as central atoms of these heteropolymolybdates. These anions are all highly oxygenated. Examples of heteropolymolybdates include $[PMo_{12}O_{40}]^3$, $[As^2Mo_{18}O_{62}]^6$, and $[TeMo_6O_{24}]^6$, where the central atoms are $P^{5+}$, $As^{5+}$, and $Te^{6+}$, respectively. A more detailed discussion of heteropolymolybdates is provided in the Kirk-Othmer Encyclopedia of Chemical Technology, 3rd ed., 15, 688–689 (1981).

Another class of heteropoly acids, which is analogous to the protonated form of heteropolymolybdates, is the protonated form of heteropolytungstates. In heteropolytungstates, the coordinating element is tungsten instead of molybdenum. U.S. Pat. No. 4,376,219, the entire disclosure of which is expressly incorporated herein by reference, discusses the preparation of various heteropoly acids. The central elements of these heteropoly acids may be selected from the group consisting of P, Si, B, Ge, As, Se, Ti, Zr, Mn, F, V, Ce, and Th. The coordinating elements of these heteropoly acids include Mo and/or W. Optional coordinating elements include V, Mn, Co, Ni, Cu, Zn, and Fe. The ratio of the number of the coordinating elements to the number of central elements may be from 2.5 to 12, preferably from 9 to 12. Particular heteropoly acids, which are exemplified in U.S. Pat. No. 4,376,219, include phosphotungstic acid, silicotungstic acid, 10-tungsto-2-vanadophosphoric acid, 6-tungsto-6-molybdophosphoric acid, phosphomolybdic acid, silicomolybdic acid, germanotungstic acid, tungstofluoric acid, and 18-tungsto-2-phosphoric acid as well as salts of all or any of these acids e.g. metal salts such as Na, K, Mg, and Ca salts. A particular heteropoly acid for use in the present invention is phosphotungstic acid, i.e., $H_3PW_{12}O_{40}$ and its metal salts particularly Na salts. Such complexing agents effectively bind to $PrP^{Sc}$.

Such chemical agents may be used alone, in combination, or with other non-bioactive chemicals such as buffers and inert binding chemicals. Heteropoly acids of the invention (e.g. PTA) are preferably, although not exclusively, used in a metallic salt form. The metallic salt includes, but is not limited to, sodium, potassium, calcium and the like.

The amount of heteropoly acid or salt thereof which is added to the serum should be an amount sufficient to significantly concentrate any $PrP^{Sc}$ present in the serum, and preferably an amount sufficient to remove $PrP^{Sc}$ to undetectable levels or at least non-infectious levels in the portion of the sample to be discarded. The weight ratio of heteropoly acid to serum may be, for example, from about 1:20 to about 1:1. The heteropoly acid may be combined with the serum in any manner which provides adequate dispersion of the heteropoly acid, thereby increasing the effective surface area of the heteropoly acid and insuring complex formation.

Biological Agents

In another embodiment, the complexing agent is a protein, peptide, or other biological moiety that selectively binds to $PrP^{Sc}$.

In one embodiment, the complexing agents are peptides or other small molecules designed to selectively bind to prions. Preferably, the peptides or small molecules are designed to preferentially bind to $PrP^{Sc}$. By "preferentially bind" is meant that the peptide is designed to be at least 20 times or more, more preferably 50 times or more, more preferably 100 times or more, and even more preferably 1000 times or more likely to bind to $PrP^{Sc}$ than to other proteins in the biological solution. Peptides of the invention are preferably designed to bind to the native form of $PrP^{Sc}$, as opposed to the denatured form, since the biological fluids generally contain $PrP^{Sc}$ in native form. Peptides may be designed to maximize binding to $PrP^{Sc}$ by designing the peptides to areas of $PrP^{Sc}$ that are more accessible to binding, as can be predicted by one skilled in the art. Useful antibodies which bind $PrP^{Sc}$ are disclosed and described in U.S. Pat. No. 5,846,533 issued Dec. 8, 1998 incorporated herein to disclose and describe antibodies and methods of making antibodies. Alternatively, peptides may be designed to bind selectively to $PrP^C$ or to both $PrP^{Sc}$ and $PrP^C$.

The complexing agent of the invention may also be an antibody selective for prions. This antibody may be added to the serum in a manner which allows for the antibody to bind the protein of interest. That antibody may bind to $PrP^{Sc}$, e.g. the antibody disclosed in U.S. Pat. No. 5,846,533. To remove $PrP^C$ present in the sample, an antibody which binds selectively or exclusively to $PrP^C$ may be used. Such an antibody is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference. The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies which bind to either $PrP^C$ or $PrP^{Sc}$ are disclosed in U.S. Pat. No. 5,846,533. Any antibody binding to $PrP^C$ and not to $PrP^{Sc}$ can be used, and those skilled in the art can generate such using known procedures, e.g., see methods of producing phage display antibody libraries in U.S. Pat. No. 5,223,409. Polyclonal anti-PrP antibodies have though been raised in rabbits following immunization with large amounts of formic acid or SDS-denatured SHaPrP 27–30 [Bendheim, Barry et al. (1984) *Nature* 310:418–421; Bode, Pocchiari et al. (1985) *J Gen Virol* 66:2471–2478; Safar, Ceroni et al. (1990) *Neurology* 40:513–517]. Similarly, a handful of anti-PrP monoclonal antibodies against PrP 27–30 have been produced in mice [Barry and Prusiner (1986) *J Infect Dis* 154:518–521; Kascsak, Rubenstein et al. (1987) *J Virol* 61:3688–3693]. These antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) *Proc Natl Acad Sci USA* 90:3182–3186].

For purposes of the invention an indication that no binding occurs means that the equilibrium or affinity constant $K_a$ is $10^6$ l/mole or less. Further, binding will be recognized as existing when the $K_a$ is at $10^7$ l/mole or greater, preferably $10^8$ l/mole or greater. The binding affinity of $10^7$ l/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

PROTEIN DETECTION ASSAYS

Once a sample is prepared in accordance with the present invention the sample may be assayed by a variety of known techniques. The examples and comparative examples put forth herein utilize a conformation-dependent immunoassay (CDI) of the type which is disclosed and described within PCT Publication WO 98/37411 published Feb. 20, 1998. However, other types of protein detection assays could be utilized. For example, it would be possible to utilize bioassays or more specifically transgenic mice which are engineered for the detection of prions. Such mice are disclosed within U.S. Pat. No. 5,565,186 issued Oct. 15, 1996; U.S. Pat. No. 5,763,740 issued Jun. 9, 1998; and U.S. Pat. No. 5,792,901 issued Aug. 11, 1998. Alternatively, the prepared sample can be assayed using antibodies of the type disclosed and described within U.S. Pat. No. 5,846,533 issued Dec. 8, 1998. Each of these publications is incorporated herein by reference in its entirety in order to disclose and describe specific types of assays which might be used on the samples prepared in accordance with the present invention. However, it is pointed out that the present invention is not limited to the use of such protein assay methodology. Other assays could be used and other assays will, no doubt, be developed which could utilize the samples prepared in accordance with the present invention in order to obtain accurate results.

Because of the high sensitivity of the conformation-dependent immunoassay the examples described herein use this assay and use it in the same way with each example tested thereby making it possible to compare results. Although the details of the assay are described within published PCT application WO 98/37411 the basic methodology will now be described.

The method requires beginning with a sample which is divided into two portions. The first portion of the sample is contacted with a binding partner. The binding partner has a higher affinity for the first conformation of the protein than it has for the second pathogenic conformation of the protein. The binding partner is typically an antibody such as labeled 3F4. After allowing the binding partner to bind to a protein in the first conformation the concentration of the binding partner/protein complexes formed is determined.

A second portion of the sample is then treated in a manner which causes the binding affinity of the protein in the second conformation to be enhanced with respect to the binding partner. This treatment can include a variety of different methodologies and often involves exposure of the sample to a protease for a sufficient period of time under sufficient conditions so as to cause the protein in the second pathogenic conformation to become more relaxed and therefor more likely to bind to the binding partner.

The treated second portion is then brought into contact with the binding partner. After binding between the proteins and binding partners are allowed to occur the concentration of binding partner/protein complexes formed in this second treated portion is determined.

If the sample contained no protein in the second, pathogenic conformation of the protein then the treatment will have little effect. However, the treatment will have some effect on the first conformation of the protein and is likely to increase it's binding affinity to the binding partner in some small degree. Accordingly, an adjustment must be made in the second concentration in order to provide an adjusted concentration which adjustment compensates for the increased affinity of the protein of the first conformation for the binding partner resulting from the treatment.

After obtaining the first concentration and the adjusted concentration the two are compared to each other. If the adjusted concentration is greater than the first concentration such is an indication of the presence of protein in the second pathogenic conformation in the original sample.

It is possible to carry out variations on the confirmation-dependent immunoassay. One variation which is described in detail in published PCT application WO 98/37411 does not require that the original sample be broken into first and second portions. The treatment process is carried out on a sample and the concentration is determined. That concentration is then compared with a known standard (previously obtained on a statistically significant group of samples) in order to determine if the sample being tested contains prions.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Comparative Example 1, 2 and 3 show that when samples containing prions are prepared respectively from (1) white blood cells, (2) platelets and (3) plasma each shows a false negative result. However, when the sample is prepared in accordance with the present invention (Example 4) from serum true positive results are obtained. In each of the comparative Examples 1, 2, 3 and in Example 4 the complexing agent used was sodium phosphotungstate. Further, each of the prepared samples was tested using a Conformation-Dependent Immunoassay (CDI).

Comparative Examples

Figure 1:
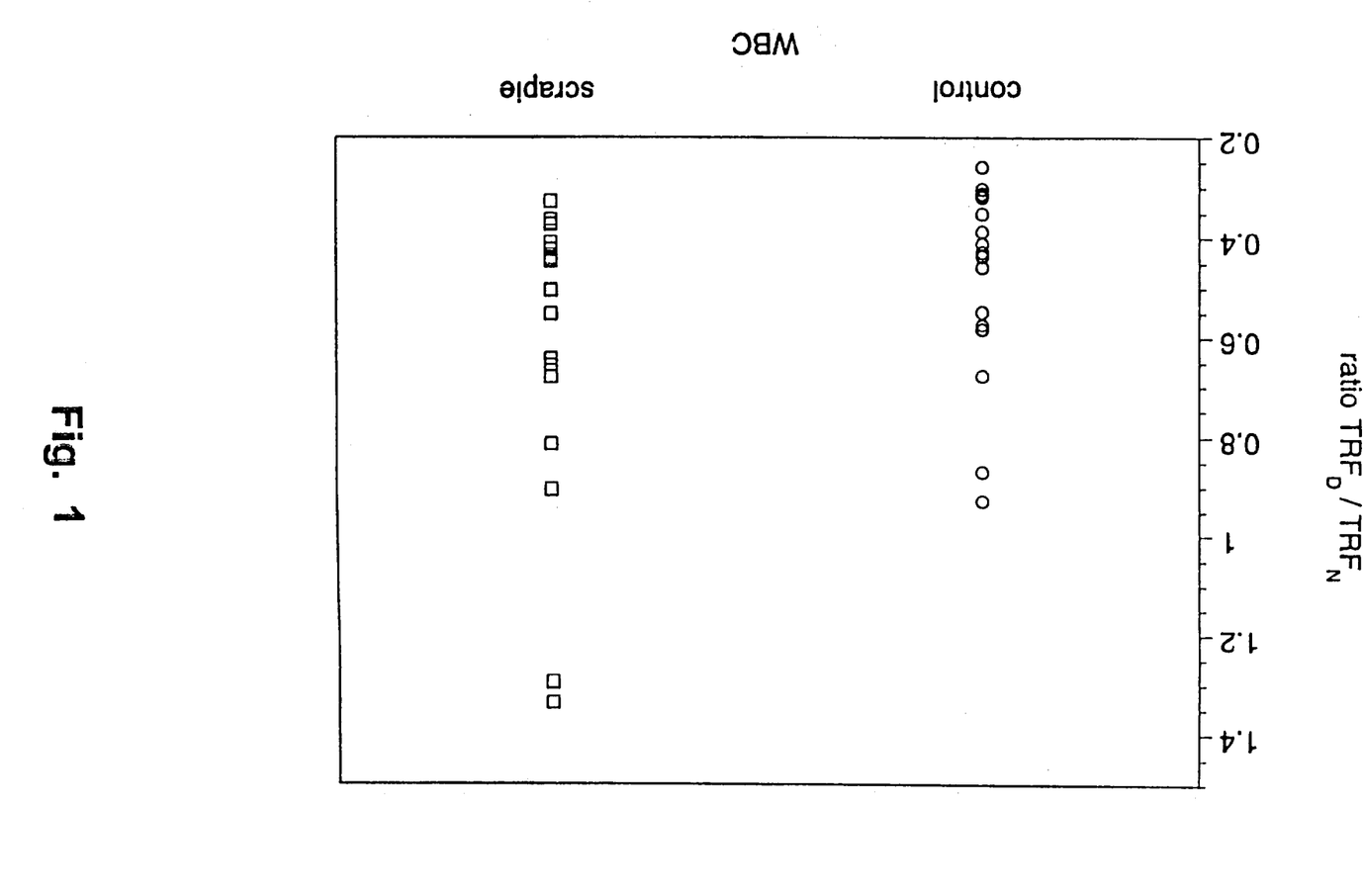
FIG. 1 is a graph showing the results of carrying out a conformation-dependent immunoassay on white blood cells from a control which do not include prions and white blood cells collected from animals that are infected with prions labeled "scrapie." The procedure and results are described in Comparative Example 1.
Figure 2:
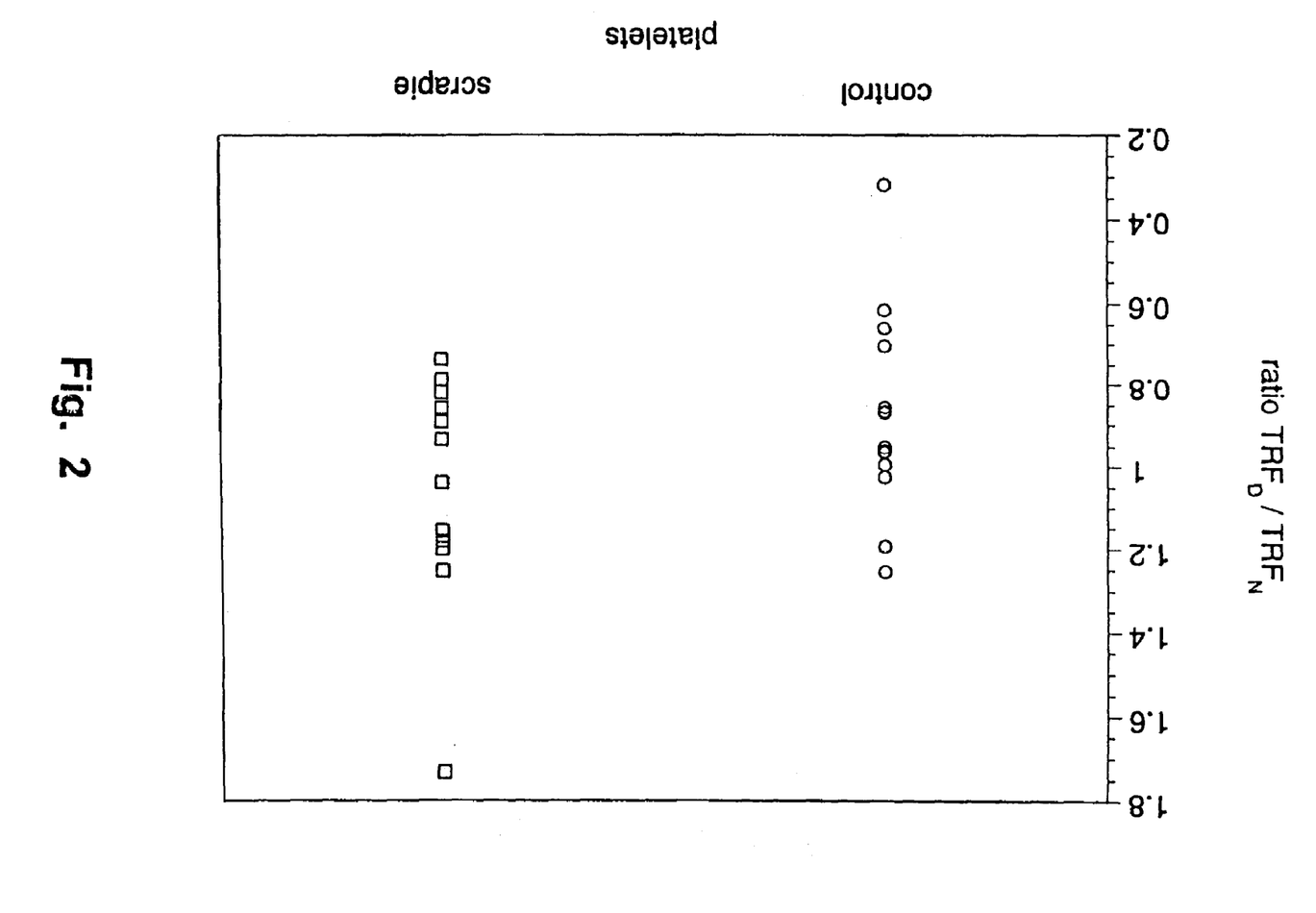
FIG. 2 is a graph showing the results of a conformation-dependent immunoassay being carried out on platelets from controls which do not include prions and samples of platelets collected from animals that are infected with prions labeled "scrapie." The procedures and results are described in Comparative Example 2.
Figure 4:
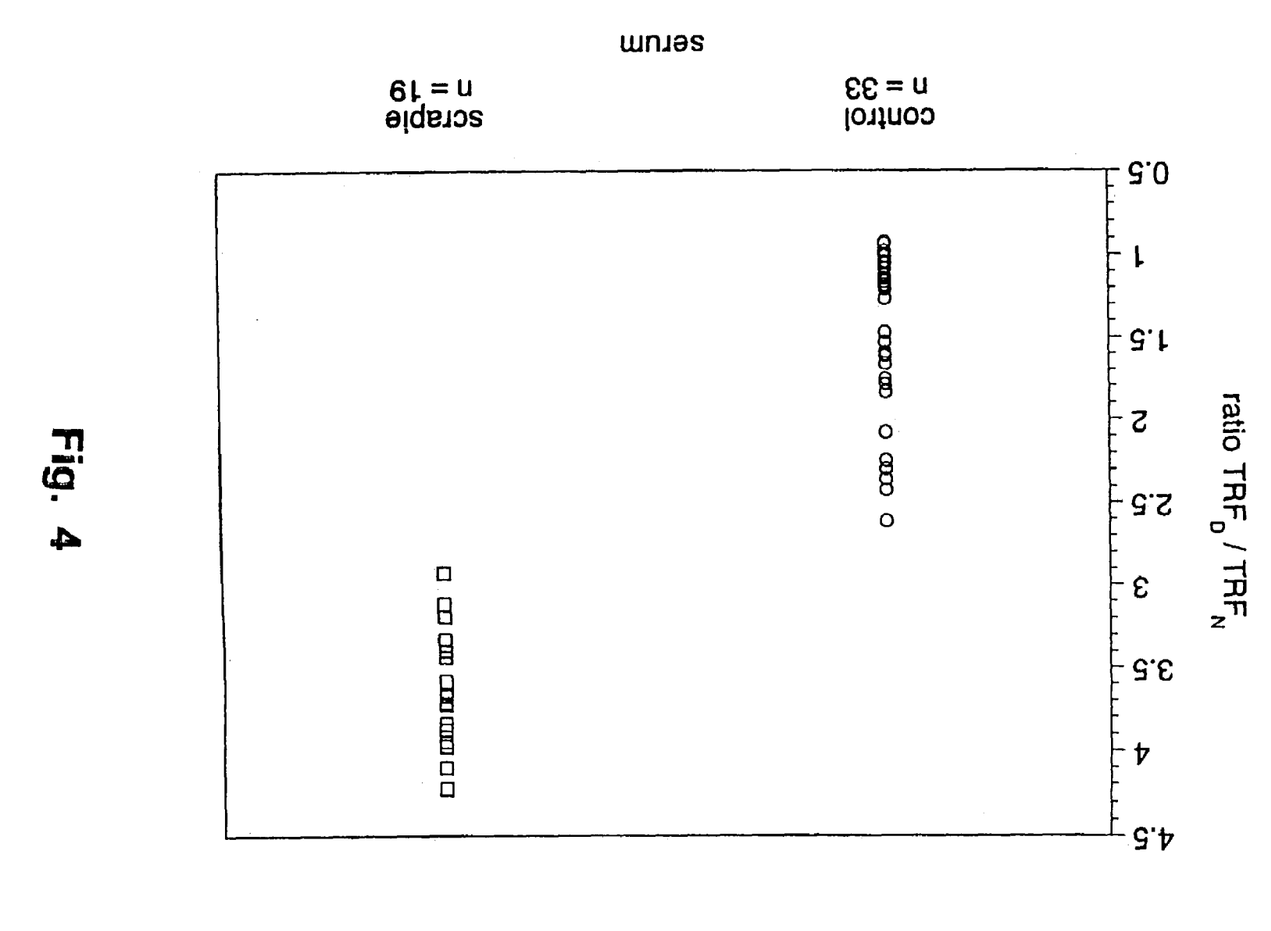
FIG. 4 is a graph showing the results of a conformation-dependent immunoassay being carried out on samples of serum prepared in accordance with the procedures of the present invention. The assay was carried out on controls which did not contain prions. The same assay was carried out on serum which was collected from animals that are infected with prions and is labeled in FIG. 4 as "scrapie." The experiment and results are further described in Example 4.
Figure 5:
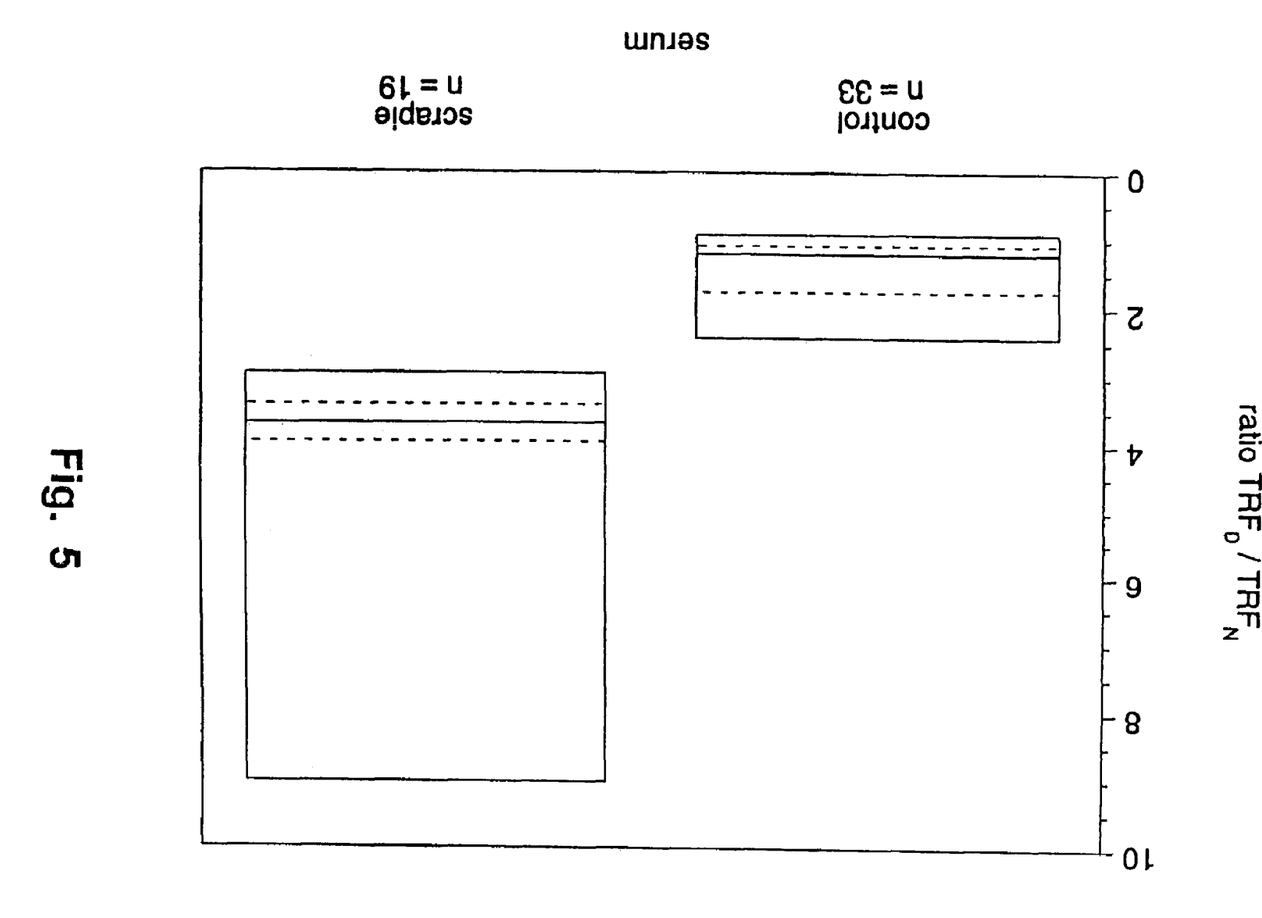
FIG. 5 is a graph which incorporates the data generated in Example 4 and shown in FIG. 4. The graph shows a median (middle line) the 50th percentile (dotted lines) and the 95th percentile (the outer box lines). The data clearly show that the control serum tested and the prion infected sample tested do not overlap.

Conformation-Dependent Immunoassay (CDI) for PrP$^{Sc}$ in Fractions of Syrian Hamster Blood Treated with Sodium Citrate To prevent coagulation, whole Syrian hamster blood was mixed (1:9) with 3.8% (w/v) buffered sodium citrate, pH 7.2, and spun 1100 RPM to obtain plasma and then separated into different fractions by Percoll gradient (Pharmacia). The white blood cells (WBC), platelets, and plasma obtained from normal (control) and scrapie-infected (scrapie) Syrian hamster blood were them precipitated with PTA in the presence of protease inhibitors. The pellet was tested by CDI for the presence of the infectious isoform of the prion protein ($PrP^{Sc}$). The sodium citrate is added to prevent clot formation and provide Comparative Examples Comparative Example 1

White Blood Cells $PrP^{Sc}$ is undetectable in white blood cells (WBC) of scrapie-infected Syrian hamsters. The WBC obtained from citrated blood were lysed in 2% Sarcosyl and precipitated with sodium phosphotungstate. The native and denatured aliquots from each sample were crosslinked to glutaraldehyde-activated ELISA plate and both aliquots were incubated with Europium labeled 3F4 monoclonal antibodies. After 7 washing steps, the signal was evaluated with Discovery (Packard Inc.) time-resolved fluorescence spectroscopy. The results are expressed as a ratio of the signals from denatured ($TRF_D$) and native ($TRF_N$) aliquots of each sample.

Comparative Example 2

Platelets $PrP^{Sc}$ is undetectable in platelets isolated from citrated blood of scrapie-infected Syrian hamsters. The platelets obtained from citrated blood were lysed in 2% Sarkosyl and precipitated with sodium phosphotungstate. The native and denatured aliquots from each sample were crosslinked to glutaraldehyde-activated ELISA plate and both aliquots were incubated with Europium labeled 3F4 monoclonal antibodies. After 7 washing steps, the signal was evaluated with Discovery (Packard Inc.) time-resolved fluorescence spectroscopy. The results are expressed as a ratio of the signals from denatured ($TRF_D$) and native ($TRF_N$) aliquots of each sample.

Comparative Example 3

Plasma $PrP^{Sc}$ is undetectable in plasma obtained from citrated blood of scrapie-infected Syrian hamsters. The plasma obtained from citrated blood was mixed with 2% Sarkosyl and precipitated with sodium phosphotungstate. The native and denatured aliquots from each sample were crosslinked to glutaraldehyde-activated ELISA plate and both aliquots were incubated with Europium labeled 3F4 monoclonal antibodies. After 7 washing steps, the signal was evaluated with Discovery (Packard Inc.) time-resolved fluorescence spectroscopy. The results are expressed as a ratio of the signals from denatured ($TRF_D$) and native ($TRF_N$) aliquots of each sample.

Example 4

Conformation-Dependent Immunoassay (CDI) for $PrP^{Sc}$ in Serum from Clotted Whole Blood Positive detection of $PrP^{Sc}$ in serum of scrapie-infected Syrian Hamsters. Values exceeding −2.5 indicate the presence of $PrP^{Sc}$ in serum. The Syrian hamster blood obtained from normal (control) or scrapie-infected Syrian hamsters (scrapie) was clotted in glass tubes (Becton-Dickinson, Inc). Serum was separated from the clot by centrifugation at 3,000 rpm and blocked with protease inhibitors. After adding 2% Sarkosyl, 0.8–1.2% (w/v) sodium phosphotungstate, and 35–50 mM $MgCl_2$, samples were incubated overnight at 37° C. and spun at 14,000 g. The pellet was resuspended and divided into native and denatured aliquots. Each aliquot was crosslinked to glutaraldehyde-activated ELISA plate and incubated with Europium labeled 3F4 monoclonal antibodies. After 7 washing steps, the signal was evaluated with Discovery (Packard Inc.) time-resolved fluorescence spectroscopy. The results are expressed as a ratio of the signals from denatured ($TRF_D$) and native ($TRF_N$) aliquots of each sample. Each data point represents single experiment.

Example 5

High diagnostic sensitivity and specificity of the serum $PrP^{Sc}$ test is demonstrated by no overlapping data from control and scrapie infected Syrian hamsters. The data from plot 4 are expressed as the median (middle line), the 50th (dotted lines), and the 95th (outer box lines) percentiles.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of concentrating a PrP protein present in a serum sample for the purpose of analysis, comprising the steps of:

allowing blood extracted from an animal to clot;

separating serum comprising PrP protein away from the clotted blood;

contacting the separated serum with a complexing agent which forms a complex with a pathogenic conformation of the PrP protein present in the serum;

concentrating the complex to thus form a sample having a concentrated pathogenic conformation of the PrP protein for use in analysis.

2. The method of claim 1, wherein the complexing agent is chosen from a heteropoly acid and a salt thereof.

3. The method of claim 1 wherein the serum is separated using centrifugation.

4. The method of claim 1, wherein the blood is obtained from a mammal selected from the group consisting of a human, a cow and a sheep not exhibiting symptoms of diseases and wherein the complexing agent is a salt of phosphotungstic acid.

5. The method of claim 1, wherein the blood is human, the concentrated pathogenic conformation of the PrP protein is PrPSC and the complexing agent is sodium phosphotungstate.

6. The method of claim 1, further comprising:
analyzing the pathogenic conformation of the PrP protein in the complex to determine characteristics.

7. The method of claim 6, wherein the characteristics are selected from the group consisting of solubility, three-dimensional structure and infectivity.

8. The method of claim 1, wherein the blood is extracted from a cow, the serum is separated using centrifugation and the complexing agent is a salt of phosphotungstic acid.

9. A method of claim 1, further comprising:
treating the sample to convert the pathogenic conformation of the PrP protein into a binding conformation having an affinity for a labeled binding partner higher than the pathogenic conformation of the PrP protein prior to treating;
contacting the treated sample with the labeled binding partner to determine a concentration of the treated pathogenic conformation of PrP protein bound to the binding partner in the sample;
adjusting the concentration to provide an adjusted concentration which compensates for increased affinity of a non-pathogenic conformation of the PrP protein to the binding partner resulting from the treating; and
comparing said adjusted concentration to a known concentration determined from a treated non-infected control sample to determine the presence of the protein in the pathogenic conformation of the PrP protein in the sample.

10. The method of claim 9, wherein said labeled binding partner comprises a labeled antibody, the complexing agent comprises a metal salt of phosphotungstic acid, and wherein the concentration is determined using flow cytometry.

11. The method of claim 9, wherein the blood is extracted from a cow, the serum is separated using centrifugation and the complexing agent is a salt of phosphotungstic acid.

12. The method of claim 9, wherein the protein in the pathogenic conformation of the PrP protein is present in the sample in a concentration of $1 \times 10^3$ protein molecules or less per ml and wherein the protein in the non-pathogenic conformation of PrP protein is present in the sample in a concentration of $1 \times 10^6$ protein molecules or more per ml.

13. The method of claim 10, wherein the antibody is 3F4 and the complexing agent is sodium phosphotungstate.

14. A method of claim 1, further comprising:
treating the sample to convert the pathogenic conformation of the PrP protein into a binding conformation having an affinity for a labeled binding partner higher than the pathogenic conformation of the PrP protein prior to treating;
contacting the treated sample with the labeled binding partner to determine a concentration of treated pathogenic conformation of PrP protein bound to the binding partner in the sample;
adjusting the concentration to provide an adjusted concentration which compensates for increased affinity a non-pathogenic conformation of the PrP protein to the binding partner resulting from the treating; and
comparing said adjusted concentration to a known concentration determined from a treated sample from a non-infected population of mammals selected from the group consisting of humans, cows and sheep to determine the presence of the protein in the pathogenic conformation of the PrP protein in the sample.

15. The method of claim 14, wherein the blood is extracted from a cow, the serum is separated using centrifugation and the complexing agent is a salt of phosphotungstic acid.

* * * * *